US008467995B2

(12) United States Patent
Lim et al.

(10) Patent No.: US 8,467,995 B2
(45) Date of Patent: Jun. 18, 2013

(54) UNIVERSAL ADAPTER FOR PERSONAL HEALTH DEVICE STANDARDIZATION OF NON-STANDARDIZED HEALTHCARE DEVICE AND OPERATING METHOD THEREOF

(75) Inventors: Joon Ho Lim, Daejeon (KR); Chan Yong Park, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 324 days.

(21) Appl. No.: 12/892,857

(22) Filed: Sep. 28, 2010

(65) Prior Publication Data

US 2011/0077910 A1     Mar. 31, 2011

(30) Foreign Application Priority Data

Sep. 29, 2009   (KR) ........................ 10-2009-0092263

(51) Int. Cl.
*G06F 15/00* (2006.01)
(52) U.S. Cl.
USPC .................... 702/188; 705/2; 705/3; 600/300; 600/365; 604/66
(58) Field of Classification Search
USPC ...... 702/188; 705/2, 3; 600/300, 365; 604/66
See application file for complete search history.

(56) References Cited

U.S. PATENT DOCUMENTS

| 7,713,173 | B2* | 5/2010 | Shin et al. .......................... 482/8 |
|---|---|---|---|
| 7,827,234 | B2* | 11/2010 | Eisenberger et al. ......... 709/203 |
| 8,095,387 | B2* | 1/2012 | Nicholson et al. ................ 705/3 |
| 2004/0186746 | A1* | 9/2004 | Angst et al. ....................... 705/3 |
| 2005/0216313 | A1* | 9/2005 | Claud et al. ....................... 705/3 |
| 2005/0273367 | A1* | 12/2005 | Nourie et al. ..................... 705/3 |
| 2006/0136014 | A1* | 6/2006 | Simms ........................... 607/60 |
| 2006/0155578 | A1* | 7/2006 | Eisenberger et al. ............. 705/2 |
| 2007/0123391 | A1* | 5/2007 | Shin et al. ......................... 482/8 |
| 2007/0214002 | A1* | 9/2007 | Smith et al. ...................... 705/2 |
| 2008/0004904 | A1* | 1/2008 | Tran ................................. 705/2 |
| 2008/0046292 | A1* | 2/2008 | Myers et al. ...................... 705/3 |
| 2009/0157426 | A1* | 6/2009 | Malec et al. ...................... 705/3 |
| 2009/0164237 | A1* | 6/2009 | Hunt et al. ........................ 705/2 |
| 2009/0164248 | A1* | 6/2009 | Hunt et al. ........................ 705/3 |
| 2009/0164249 | A1* | 6/2009 | Hunt et al. ........................ 705/3 |

FOREIGN PATENT DOCUMENTS

KR    10-2002-0020137 A    3/2002

* cited by examiner

*Primary Examiner* — Carol Tsai

(57) ABSTRACT

Disclosed are a universal adapter for the personal health device (PHD) standardization of a non-standardized healthcare device and an operating method thereof. The universal adapter includes: an adapter interface device communicating with a non-standardized healthcare device, which does not follow PHD standardization, to collect measurement data measured by the non-standardized healthcare device; and a universal adapter device receiving the measurement data from the adapter interface device, generating a PHD standard message including the received measurement data, and transmitting the PHD standard message to a PHD gateway according to a PHD standard communication scheme.

11 Claims, 2 Drawing Sheets

UNIVERSAL ADAPTER FOR PERSONAL HEALTH DEVICE STANDARDIZATION OF NON-STANDARDIZED HEALTHCARE DEVICE AND OPERATING METHOD THEREOF

CROSS-REFERENCE TO RELATED APPLICATIONS

This application claims the priority of Korean Patent Application No. 10-2009-0092263 filed on Sep. 29, 2009, in the Korean Intellectual Property Office, the disclosure of which is incorporated herein by reference.

BACKGROUND OF THE INVENTION

1. Field of the Invention

The present invention relates to a universal adapter for the personal health device (PHD) standardization of a non-standardized healthcare device and an operating method thereof, and more particularly, to a technique for easily developing a PHD standard compatible healthcare device by using a non-standardized healthcare device.

2. Description of the Related Art

Conventional healthcare devices use a data format and a communication method individually defined by each vendor, so therefore, healthcare devices manufactured by different vendors are not compatible with each other.

Thus, an SO/IEEE 11073 PHD (Personal Health Device) international standard (hereinafter, referred to as a 'PHD standard') was developed in order to overcome the incompatibility between healthcare devices and provide interoperability between healthcare devices manufactured by different vendors.

However, domestic healthcare device manufacturers, a majority of which are small and medium enterprises, lack the capability to accept this standardization and incorporate it into the manufacturing of healthcare devices. Thus, a technique for allowing those small businesses to easily manufacture PHD standard-compatible healthcare devices is required.

SUMMARY OF THE INVENTION

An aspect of the present invention provides a universal adapter for the personal health device (PHD) standardization of a non-standardized healthcare device and an operating method thereof capable of easily developing a PHD standard compatible healthcare device by using a non-standardized healthcare device.

According to an aspect of the present invention, there is provided a universal adapter for the personal health device (PHD) standardization of a non-standardized healthcare device, including: an adapter interface device communicating with a non-standardized healthcare device, which does not follow PHD standardization, to collect measurement data measured by the non-standardized healthcare device; and a universal adapter device receiving the measurement data from the adapter interface device, generating a PHD standard message including the received measurement data, and transmitting the PHD standard message to a PHD gateway according to a PHD standard communication scheme.

The adapter interface device may include: a healthcare device interface module receiving the measurement data from the non-standardized healthcare device; a communication module receiving the measurement data from the healthcare device interface module and transmitting the received measurement data to the universal adapter device; and a control module controlling operations of the healthcare device interface module and the communication module.

The communication module may perform communication according to an adapter protocol previously defined for communications between the adapter interface device and the universal adapter device.

The adapter protocol may perform communication through a message of a predetermined size including a type of the non-standardized healthcare device, a type of the measurement data, the measurement data, and data measurement time information.

The universal adapter device may include: an adapter interface communication module receiving the measurement data from the adapter interface device; a PHD standard communication module generating a PHD standard message including the measurement data received from the adapter interface communication module, and transmitting the PHD standard message to the PHD gateway according to the PHD standard communication scheme; and a control module controlling operations of the adapter interface communication module and the PHD standard communication module.

The adapter interface communication module may perform communication according to an adapter protocol previously defined for communications between the adapter interface device and the universal adapter device.

The PHD standard communication module may generate the PHD standard message by using a PHD message template.

The PHD message template may be generated by using the information regarding the type of the non-standardized healthcare device and the type of the measurement data.

The PHD standard communication module may generate the PHD standard message by merging the measurement data which has been transferred from the adapter interface communication module with the PHD message template.

According to another aspect of the present invention, there is provided a method for operating a universal adapter, including an adapter interface device and an universal adapter device, for personal health device (PHD) standardization of a non-standardized healthcare device, including: receiving, by the universal adapter device, measurement data measured by a non-standardized healthcare device from the adapter interface device; generating a PHD standard message including the measurement data; and transmitting the measurement data to a PHD gateway through the generated PHD standard message according to a PHD standard communication scheme.

In generating the PHD standard message, the PHD standard message may be generated by merging the measurement data and a PHD message template.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
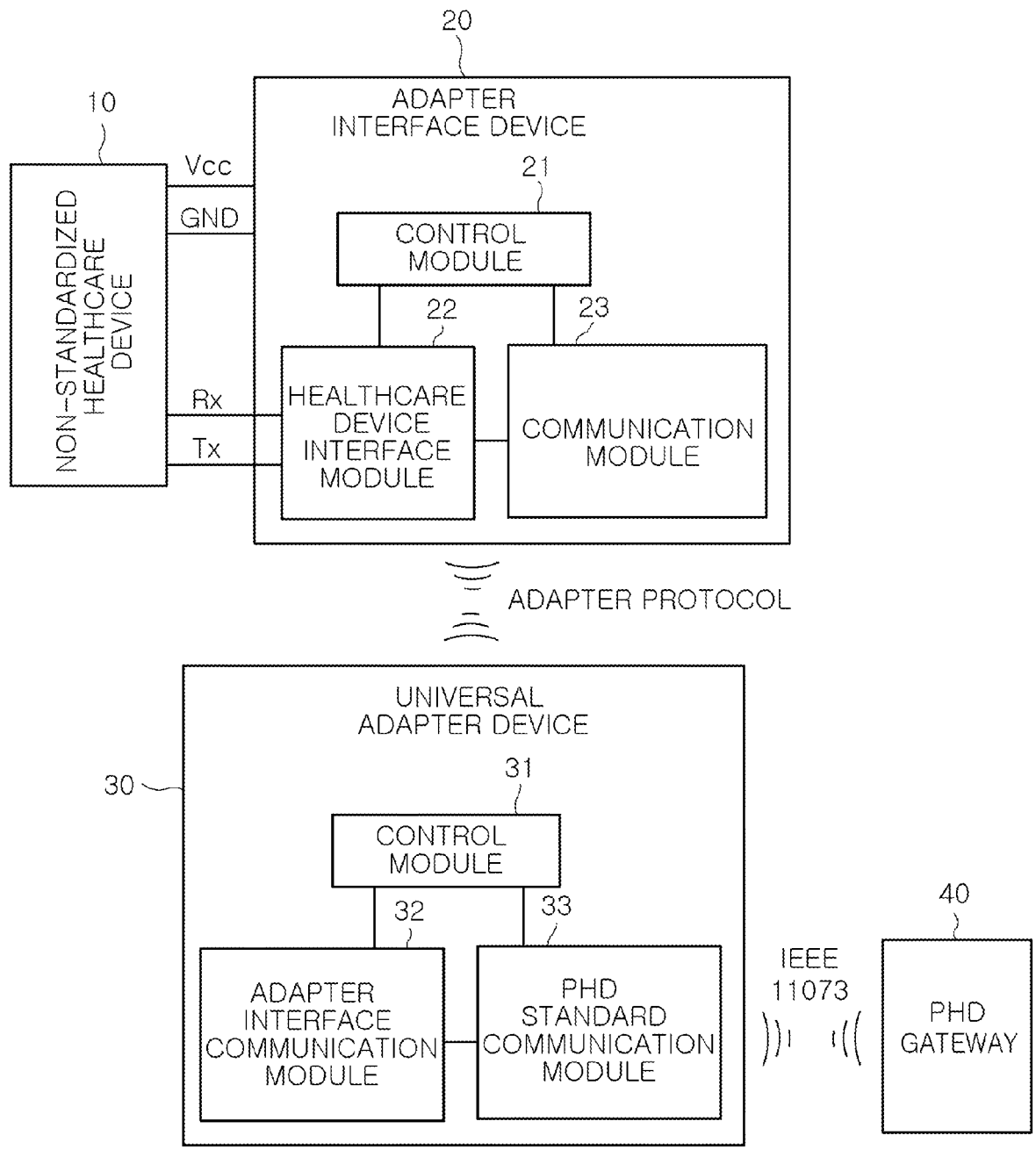
FIG. 1 is a schematic block diagram of a universal adapter for the personal health device (PHD) standardization of a non-standardized healthcare device according to an exemplary embodiment of the present invention.

Exemplary embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In describing the present invention, if a detailed explanation for a related known function or construction is considered to unnecessarily divert from the gist of the present invention, such explanation will be omitted but would be understood by those skilled in the art.

In the drawings, the shapes and dimensions may be exaggerated for clarity, and the same reference numerals will be used throughout to designate the same or like components.

When a component is mentioned as being "connected" to or "accessing" another component, this may mean that it is directly connected to or accessing the other component, but it is to be understood that another component may exist there between. Also, unless explicitly described to the contrary, the word "comprise" and variations such as "comprises" or "comprising," will be understood to imply the inclusion of stated elements but not the exclusion of any other elements.

The term 'module' refers to a unit for performing a particular function or operation, which can be implemented by hardware, software, or a combination of hardware and software.

FIG. 1 is a schematic block diagram of a universal adapter for the personal health device (PHD) standardization of a non-standardized healthcare device according to an exemplary embodiment of the present invention.

A universal adapter for the PHD standardization of a non-standardized healthcare device according to an exemplary embodiment of the present invention includes an adapter interface device 20 and a universal adapter device 30.

The adapter interface device 20 communicates with a non-standardized healthcare device 10 that does not follow a PHD standard to collect data measured by the non-standardized healthcare device 10, and transmits the collected data to the universal adapter device 30.

The adapter interface device 20 includes a control module 21, a healthcare device interface module 22, and a communication module 23.

The control module 21 controls the operations of the elements included in the adapter interface device 20.

The healthcare device interface module 22, serving to provide an interface between the adapter interface device 20 and the non-standardized healthcare device 10, receives measurement data (Rx, Tx) transmitted from the non-standardized healthcare device 10. In this case, in order to perform communication with various non-standardized healthcare devices 10 using different data formats and communication methods, the healthcare device interface module 22 is implemented based on a communication scheme suitable for each of the non-standardized healthcare devices 10.

The communication module 23 transmits the measurement data transferred from the healthcare device interface module 22 to the universal adapter device 30 according to an adapter protocol defined for communications between the adapter interface device 20 and the universal adapter device 30. In this case, the adapter protocol performs communication by using a message having a predetermined size, and the message may include information such as a type of a healthcare device, a type of measurement data, a measurement value, a measurement time, and the like. The communication module 23 may be implemented based on a radio communication technique such as, for example, ZigBee™ or Bluetooth™.

The adapter interface device 20 may be included in the non-standardized healthcare device 10 or attached to the exterior of the non-standardized healthcare device 10 to provide a minimum data interface with the non-standardized healthcare device 10.

The universal adapter device 30 receives the measurement data measured by the non-standardized healthcare device 10 from the adapter interface device 20, generates a PHD standard message including the received measurement data, and then transmits the generated PHD standard message to a PHD gateway 40 according to a PHD standard communication scheme.

The universal adapter device 30 includes a control module 31, an adapter interface communication module 32, and a PHD standard communication module 33.

The control module 31 controls the operations of the respective elements included in the universal adapter device 30.

The adapter interface communication module 32 communicates with the adapter interface device 20 according to the foregoing adapter protocol to receive the measurement data transmitted from the adapter interface device 20. Like the communication module 23 included in the adapter interface device 20, the adapter interface communication module 32 may also be implemented based on the radio communication technique such as ZigBee™ or Bluetooth™.

The PHD standard communication module 33 generates a PHD standard message including the measurement data transferred from the adapter interface communication module 32, and transmits the generated PHD standard message to the PHD gateway 40 according to the PHD standard communication scheme.

In this case, the PHD standard communication module 33 may generate the PHD standard message by using a PHD message template. Here, the PHD message template may be appropriately generated by using information such as the type of the non-standardized healthcare device 10 used for the data measurement, the type of the measurement data, and the like. For example, the PHD message template may be generated by a program called a PHE message builder. The following is an example of a PHD message template with respect to a weighing scale device.

```
<PHD_Messages>
    <association>
        <request length="54">
            <base>0xE2 0x00 0x00 0x32 0x80 0x00 0x00 0x00 0x00 0x01 0x00 0x2A 0x50
0x79 0x00 0x26 0x80 0x00 0x00 0x00 0xA0 0x00 0x80 0x00 0x00 0x00 0x00 0x00 0x00
0x00 0x00 0x80 0x00 0x00 0x00 0x08 0x11 0x22 0x33 0x44 0x55 0x66 0x77 0x88 0x40
0x00 0x00 0x01 0x01 0x00 0x00 0x00 0x00 0x00</base>
            <changeValueList>
                <changeValue startPos="1" size="0" type="data-proto-id"/>
            </changeValueList>
        </request>
        <response type="normal" length="48">
            <base>0xE3 0x00 0x00 0x2C 0x00 0x03 0x50 0x79 0x00 0x26 0x80 0x00 0x00
0x00 0x80 0x00 0x80 0x00 0x00 0x00 0x00 0x00 0x00 0x00 0x80 0x00 0x00 0x00 0x00
0x08 0x88 0x77 0x66 0x55 0x44 0x33 0x22 0x11 0x00 0x00 0x00 0x00 0x00 0x00 0x00
0x00 0x00 0x00</base>
        </response>
    </association>
    <configuration>
        <request data="fixed" length="0">
            <base>0xE7 0x00 0x00 0xA2 ... 0x0A 0x56 0x00 0x04 0x09 0x90 0x00 0x08
</base>
            <changeValue startPos="14" size="2" type="invoke-id"/>
        </request>
        <response type="accepted-config" length="26">
            <base>0xE7 0x00 0x00 0x16 0x00 0x14 0x12 0x35 0x02 0x01 0x00 0x0E 0x00
0x00 0x00 0x00 0x00 0x00 0x0D 0x1C 0x00 0x04 0x40 0x00 0x00 0x00</base>
        </response>
        <response type="unknown-config" length="26">
            <base>0xE7 0x00 0x00 0x16 0x00 0x14 0x12 0x35 0x02 0x01 0x00 0x0E 0x00
0x00 0x00 0x00 0x00 0x00 0x0D 0x1C 0x00 0x04 0x40 0x00 0x01 0x01</base>
        </response>
    </configuration>
    <get-mds>
        <!-- ... -->
    </get-mds>
    <reportData>
        <request data="fixed" length="113" type="Agent-initiated">
            <base>0xE7 0x00 0x00 0x6D 0x00 0x6B 0x00 0x00 0x01 0x01 0x00 0x65 0x00
0x06 0x00 0x61 0x0A 0x5A 0x00 0x00 0x08 0x00 0x00 0x01 0x00 0x04 0x10 0x0F 0x00 0x00 0x01 0x09
0x28 0x00 0x1E 0x00 0x0A 0x00 0x0A 0x54 0x68 0x65 0x43 0x6F 0x6D 0x70 0x61 0x6E
0x79 0x00 0x0C 0x00 0x0C 0x54 0x68 0x65 0x53 0x63 0x61 0x6C 0x65 0x41 0x42 0x43
0x00 0x09 0x84 0x00 0x08 0x31 0x32 0x33 0x34 0x35 0x36 0x37 0x38 0x0A 0x44 0x00
0x02 0x40 0x00 0x09 0x2D 0x00 0x11 0x00 0x01 0x00 0x0D 0x00 0x01 0x00 0x00 0x00
0x07 0x44 0x45 0x31 0x32 0x33 0x34 0x35 0x09 0x87 0x00 0x08 0x20 0x07 0x12 0x16
0x12 0x10 0x00 0x00</base>
            <changeValueList>
                <changeValue startPos="14" size="2" type="invoke-id"/>
                <changeValue startPos="22" size="4" type="device-id"/>
                <changeValue startPos="34" size="4" type="MDC_MASS_BODY_ACTUAL"/>
                <changeValue startPos="38" size="8" type="ABSOLUTE_TIME"/>
                <changeValue startPos="50" size="4" type="MDC_RATIO_MASS_BODY_LEN_SQ"/>
                <changeValue startPos="54" size="8" type="ABSOLUTE_TIME"/
            </changeValueList>
        </request>
        <response type="ack" length="22">
            <base>0xE7 0x00 0x00 0x12 0x00 0x10 0x12 0x36 0x02 0x01 0x00 0x0A 0x00
0x00 0x00 0x00 0x00 0x00 0x0D 0x1D 0x00 0x00</base>
        </response>
    </reportData>
    <disassociation>
```

```
        <request type="normal" length="6">
            <base>0xE4 0x00 0x00 0x02 0x00 0x0</base>
        </request>
        <response type="ack" length="6">
            <base>0xE6 0x00 0x00 0x02 0x00 0x00</base>
        </response>
    </disassociation>
</PHD_Messages>
```

The PHD standard communication module 33 merges the measurement data which has been transferred from the adapter interface communication module 32 with the PHD message template to generate a PHD standard message, and perform communication with the PHD gateway 40 by using the generated PHD standard message according to the PHD standard communication scheme, and in this case, the PHD standard communication module 33 transmits the measurement data through the process of requesting a connection, setting up an environment, merging the measurement data, transmitting the measurement data, releasing the connection, and the like.

Figure 2:
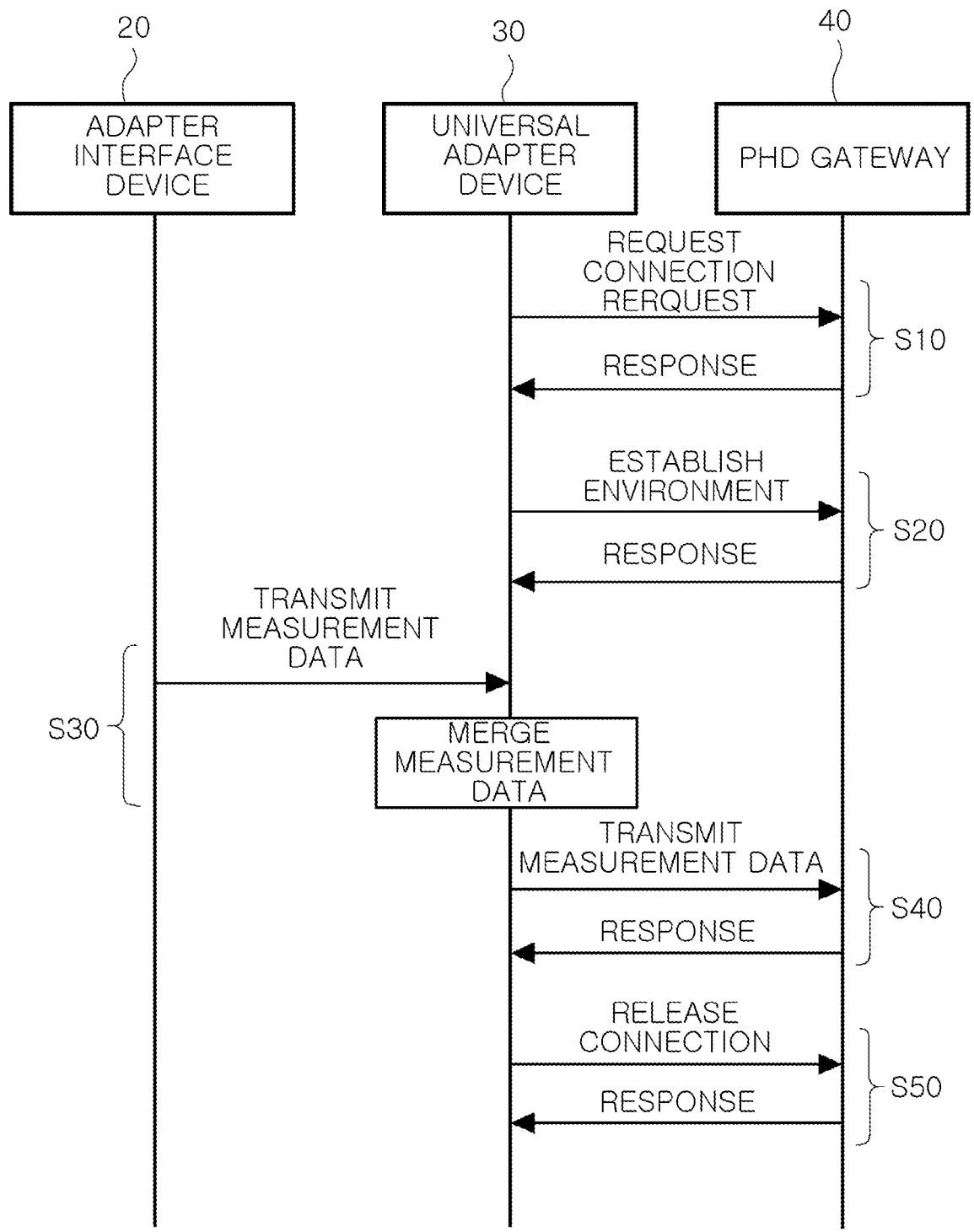
FIG. 2 is a flow chart illustrating the process of an operation of a universal adapter for the personal health device (PHD) standardization of a non-standardized healthcare device according to an exemplary embodiment of the present invention.

FIG. 2 is a flow chart illustrating the process of an operation of the universal adapter for the personal health device (PHD) standardization of a non-standardized healthcare device according to an exemplary embodiment of the present invention.

The universal adapter device 30 performs communication with the PHD gateway 40 through the process of requesting a connection (S10), setting up an environment (S20), transmitting measurement data (S40), and releasing the connection (S50). A detailed communication method follows the PHD standard, so a detailed description thereof will be omitted.

In order to transmit the measurement data, the universal adapter device 30 according to an exemplary embodiment of the present invention receives the measurement data, which has been measured by the non-standardized healthcare device connected to the adapter interface device 20, from the adapter interface device 20, merges the received measurement data with a PHD message template (e.g., using changeValue tag information) to generate a PHD standard message (S30). Thus, the universal adapter device 30 can transmit the measurement data to the PHD gateway 40 according to the PHD standard communication scheme. Also, after transmitting the measurement data, the universal adapter device 30 may determine whether or not the measurement data has been properly processed according to a corresponding device type through a received response message.

As set forth above, according to exemplary embodiments of the invention, the use of the universal adapter for PHD standardization allows for a development of a PHD standard-compatible healthcare device with ease by using a non-standardized healthcare device.

Thus, numerous enterprises or businesses can manufacture PHD standard-compatible healthcare devices at a low cost, and accordingly, a development of a healthcare system capable of collectively managing users' health by combining various healthcare devices can be promoted.

While the present invention has been shown and described in connection with the exemplary embodiments, it will be apparent to those skilled in the art that modifications and variations can be made without departing from the spirit and scope of the invention as defined by the appended claims.

What is claimed is:

1. A universal adapter for the personal health device (PHD) standardization of a non-standardized healthcare device, the adapter comprising:
    an adapter interface device configured to communicate with a non-standardized healthcare device, which does not follow PHD standardization, to collect measurement data measured by the non-standardized healthcare device; and
    a universal adapter device configured to receive the measurement data from the adapter interface device, generate a PHD standard message including the received measurement data, and transmit the PHD standard message to a PHD gateway according to a PHD standard communication scheme,
    wherein the adapter interface device comprises:
    a healthcare device interface module configured to receive the measurement data from the non-standardized healthcare device;
    a communication module configured to receive the measurement data from the healthcare device interface module and transmit the received measurement data to the universal adapter device; and
    a control module configured to control operations of the healthcare device interface module and the communication module.

2. The universal adapter of claim 1, wherein the communication module performs communication according to an adapter protocol previously defined for communications between the adapter interface device and the universal adapter device.

3. The universal adapter of claim 2, wherein communication according to the adapter protocol includes using a message of a predetermined size, the message including information including a type of the non-standardized healthcare device, a type of the measurement data, the measurement data, and data measurement time information.

4. A universal adapter for the personal health device (PHD) standardization of a non-standardized healthcare device, the adapter comprising:

an adapter interface device configured to communicate with a non-standardized healthcare device, which does not follow PHD standardization, to collect measurement data measured by the non-standardized healthcare device; and a universal adapter device configured to receive the measurement data from the adapter interface device, generate a PHD standard message including the received measurement data, and transmit the PHD standard message to a PHD gateway according to a PHD standard communication scheme, wherein the universal adapter device comprises:

an adapter interface communication module configured to receive the measurement data from the adapter interface device;

a PHD standard communication module configured to generate a PHD standard message including the measurement data received from the adapter interface communication module, and transmit the PHD standard message to the PHD gateway according to the PHD standard communication scheme; and a control module configured to control operations of the adapter interface communication module and the PHD standard communication module.

5. The universal adapter of claim 4, wherein the adapter interface communication module performs communication according to an adapter protocol previously defined for communications between the adapter interface device and the universal adapter device.

6. The universal adapter of claim 4, wherein the PHD standard communication module generates the PHD standard message by using a PHD message template.

7. The universal adapter of claim 6, wherein the PHD message template is generated by using information regarding a type of the non-standardized healthcare device and a type of the measurement data.

8. The universal adapter of claim 6, wherein the PHD standard communication module generates the PHD standard message by merging the measurement data which has been transferred from the adapter interface communication module with the PHD message template.

9. A method for operating a universal adapter, including an adapter interface device and universal adapter device, for personal health device (PHD) standardization of a non-standardized healthcare device, the method comprising:

communicating, by the adapter interface device, with the non-standardized healthcare device, which does not follow PHD standardization, to collect measurement data measured by the non-standardized healthcare device;

receiving, by the universal adapter device, measurement data measured by the non-standardized healthcare device from the adapter interface device;

generating, by the universal adapter device, a PHD standard message including the measurement data; and transmitting, by the universal adapter device, the PHD standard message to a PHD gateway according to a PHD standard communication scheme, wherein a healthcare device interface module of the adapter interface device receives the measurement data from the non-standardized healthcare device, wherein a communication module of the adapter interface device receives the measurement data from the healthcare device interface module and transmits the received measurement data to the universal adapter device, and wherein a control module is configured to control operations of the healthcare device interface module control and the communication module.

10. The method of claim 9, wherein generating the PHD standard message includes merging the measurement data and a PHD message template.

11. The method of claim 9 wherein the measurement data is transmitted from the adapter interface device to the universal adapter device according to an adapter protocol, and wherein a message according to the adapter protocol has a predetermined size, the message including a type of the non-standardized healthcare device, a type of the measurement data, the measurement data, and data measurement time information.

* * * * *